(12) United States Patent
Medford et al.

(10) Patent No.: US 11,768,131 B2
(45) Date of Patent: Sep. 26, 2023

(54) HANDS-FREE LIQUID SAMPLING METHODS AND APPARATUS

(71) Applicant: Duke Energy Corporation, Charlotte, NC (US)

(72) Inventors: Isaac John Medford, Canton, NC (US); Maverick James Raber, Stanley, NC (US); Jason Chadwick Green, Raleigh, NC (US)

(73) Assignee: Duke Energy Corporation, Charlotte, NC (US)

( * ) Notice: Subject to any disclaimer, the term of this patent is extended or adjusted under 35 U.S.C. 154(b) by 0 days.

(21) Appl. No.: 17/668,079

(22) Filed: Feb. 9, 2022

(65) Prior Publication Data

US 2023/0251169 A1   Aug. 10, 2023

(51) Int. Cl.
  *G01N 1/10*   (2006.01)
  *G01N 33/18*  (2006.01)

(52) U.S. Cl.
  CPC .............. *G01N 1/10* (2013.01); *G01N 33/18* (2013.01)

(58) Field of Classification Search
  CPC ................................ G01N 1/10; G01N 33/18
  See application file for complete search history.

(56) References Cited

U.S. PATENT DOCUMENTS

2002/0095997 A1   7/2002   Cordry

FOREIGN PATENT DOCUMENTS

| CN | 109159855 A | | 1/2019 | |
|---|---|---|---|---|
| CN | 109357913 A | | 2/2019 | |
| CN | 208607036 U | * | 3/2019 | ............. G01F 23/02 |
| CN | 112525601 A | * | 3/2021 | ............. B64C 39/02 |
| CN | 113447317 A | | 9/2021 | |
| CN | 114013572 A | | 2/2022 | |

* cited by examiner

*Primary Examiner* — Herbert K Roberts
*Assistant Examiner* — Anthony W Megna Fuentes
(74) *Attorney, Agent, or Firm* — Myers Bigel, P.A.

(57) ABSTRACT

Liquid sampling apparatus and methods enable hands free collection of low-level metals and other contaminant-sensitive samples from surface waters via drone or other remote delivery systems. The apparatus and methods allow for limited exposure to contaminants during a sampling process by remotely opening and closing sample containers while submerged under water at a sampling location.

19 Claims, 10 Drawing Sheets

HANDS-FREE LIQUID SAMPLING METHODS AND APPARATUS

FIELD OF THE INVENTION

The present invention relates generally to sampling methods and apparatus and, more particularly, to liquid sampling methods and apparatus.

BACKGROUND OF THE INVENTION

Conventional methods of sampling bodies of water for the presence of low-level (parts per trillion) mercury and other metals involve dipping a container into the water by hand or pumping water into a container using tubing at the sampling location. These conventional methods typically require a user to manually uncap and re-seal the sample containers on site. Unfortunately, manual handling of containers and atmospheric conditions can introduce contamination. Furthermore, some sampling locations, such as the middle of a river, may present a significant safety risk when accessed via traditional methods, such as wading or boating.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Liquid sampling apparatus and methods, according to embodiments of the present inventive concept, enable hands free collection of low-level metals and other contaminant-sensitive samples from surface waters via drone or other remote delivery systems. As such, clean sample collection techniques required for certain environmental evaluations using methods such as EPA 1631 (Low-Level mercury), and remote sampling platforms such as drones or extended arm samplers can be utilized. Liquid sampling apparatus according to embodiments of the present inventive concept maintain limited exposure (and enable the clean hands/dirty hands technique) to contaminants during a sampling process by remotely opening and closing sample containers while submerged under water at a sampling location.

According to some embodiments of the present inventive concept, an aerial drone flies to a designated sample area and lowers a tethered liquid sampling apparatus into the water until onboard sample bottles are fully submerged, while the float section of the device remains at the surface. A servo attached to a primary gear causes the primary gear to rotate which causes smaller gears associated with the bottle cap sockets that house the caps for the sample bottles to rotate. The sample bottles are remotely opened until the caps are removed and the sample bottles detach, filling passively. As the device is raised by the drone, the caps are lowered back onto the bottles while underwater where they are then closed via the same gear mechanism. After sampling is completed, flight operations return the device and samples back to ground crews where they can be removed from the device using clean hands/dirty hands low level sampling techniques.

Embodiments of the present invention are not limited to the use of an aerial drone for deployment. Various other ways of deploying the liquid sampling apparatus of the present invention may be utilized. For example, the liquid sampling apparatus can be deployed using a cable, a rope, a pole, or by hand, from a bridge, bank, other elevated surface, etc., without limitation.

Liquid sampling apparatus and methods, according to embodiments of the present inventive concept, are advantageous over conventional sampling apparatus and methods because they allow for sample collection in areas of restricted access and in dangerous areas that can present safety concerns for field personnel. As such, the need for wading or boat use in dangerous areas, such as a river, etc., can be eliminated.

According to some embodiments of the inventive concept, a liquid sampling apparatus includes a base having at least one bottle holder configured to removably receive a sample bottle therein. The apparatus further includes an upper portion and at least one elongate rod coupling the base and the upper portion in spaced-apart relation to each other. An intermediate portion is movably secured to the at least one elongate rod between the base and the upper portion and includes a float configured to provide buoyancy to the liquid sampling apparatus such that the liquid sampling apparatus floats on a liquid surface. The intermediate portion also includes a cap engagement apparatus configured to remove a cap from a sample bottle supported within the at least one bottle holder, and to resecure the cap to the bottle. When the liquid sampling apparatus is lowered into a body of liquid, such as water (e.g., a river, a lake, a pond, etc.), the apparatus is configured to float on the liquid surface with the base and bottle supported therein submerged beneath the liquid surface. The bottle fills with liquid in response to the cap engagement apparatus removing the cap from the bottle. In some embodiments, the base includes ballast that facilitates submerging of the base beneath the liquid surface when the cap is removed from the bottle by the cap engagement apparatus. Once the sample bottle fills with liquid, the liquid sampling apparatus is lifted from the liquid surface, for example, by hand, via a drone, etc., and the cap engagement apparatus is configured to move downwardly under the force of gravity to engage the bottle and resecure the cap to the bottle.

In some embodiments, the cap engagement apparatus includes a socket that is configured to releasably engage the cap. The socket is rotatable and is configured to threadingly remove the cap from the bottle and to threadingly resecure the cap to the bottle.

In some embodiments, the socket includes a gear that meshes with a primary gear associated with the intermediate portion such that rotation of the primary gear about its rotational axis causes the socket to rotate about its rotational axis. The intermediate portion includes an electric motor that is configured to rotate the primary gear about its rotational axis, and an electronic controller that is operable to control operation of the electric motor in response to a control signal from an input device. In some embodiments, the intermediate portion includes a communication module that is configured to receive, over a wireless link, a control signal from an input device. In some embodiments, the electric motor, the electronic controller, and any other electronics, such as the communication module, may be located within a body of the float.

In some embodiments, the liquid sampling apparatus includes a liquid detection switch that is configured to detect when the liquid sampling apparatus has been lowered into a liquid. The electronic controller is configured to control operation of the electric motor such that the cap engagement apparatus removes the cap from the bottle in response to a signal received from the liquid detection switch.

In some embodiments, the liquid sampling apparatus may include a lift detection switch that is configured to detect when the liquid sampling apparatus is lifted from the liquid. The electronic controller is configured to control operation of the electric motor such that the cap engagement apparatus resecures the cap to the bottle in response to a signal received from the lift detection switch.

According to some embodiments of the present invention, a hands-free liquid sampling method includes lowering a floatable apparatus into a liquid, wherein the apparatus includes a base supporting a sample bottle, and a cap engagement apparatus configured to remove a cap from the sample bottle and to resecure the cap to the sample bottle. Once the liquid sampling apparatus is in the liquid, the base and sample bottle are submerged and the cap from the sample bottle is removed via the cap engagement apparatus, thereby causing the bottle to fill with the liquid. The liquid sampling apparatus is then lifted from the liquid, thereby causing the cap engagement apparatus to move downwardly to engage the bottle and resecure the cap to the bottle before the bottle reaches the surface of the liquid.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

DETAILED DESCRIPTION

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. The term "and/or" includes any and all combinations of one or more of the associated listed items.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.," which derives from the Latin phrase "exempli gratia," may be used to introduce or specify a general example or examples of a previously mentioned item, and is not intended to be limiting of such item. The common abbreviation "i.e.," which derives from the Latin phrase "id est," may be used to specify a particular item from a more general recitation.

It will be understood that although the terms first, second, third, etc., may be used herein to describe various elements/ operations, these elements/operations should not be limited by these terms. These terms are only used to distinguish one element/operation from another element/operation. Thus, a first element/operation in some embodiments could be termed a second element/operation in other embodiments without departing from the teachings of present inventive concept.

The terms "about" and "approximately", as used herein with respect to a value or number, means that the value or number can vary by +/− twenty percent (20%).

Embodiments of the present inventive concept can be utilized to collect samples from any liquid body. Embodiments are not limited to just the sampling of water. As such, embodiments of the present inventive concept can be used in virtually any situation where a hands-free sampling of liquid is required from a large volume of the liquid and where it would be dangerous and/or difficult to use conventional sampling apparatus and methods.

Figure 1:
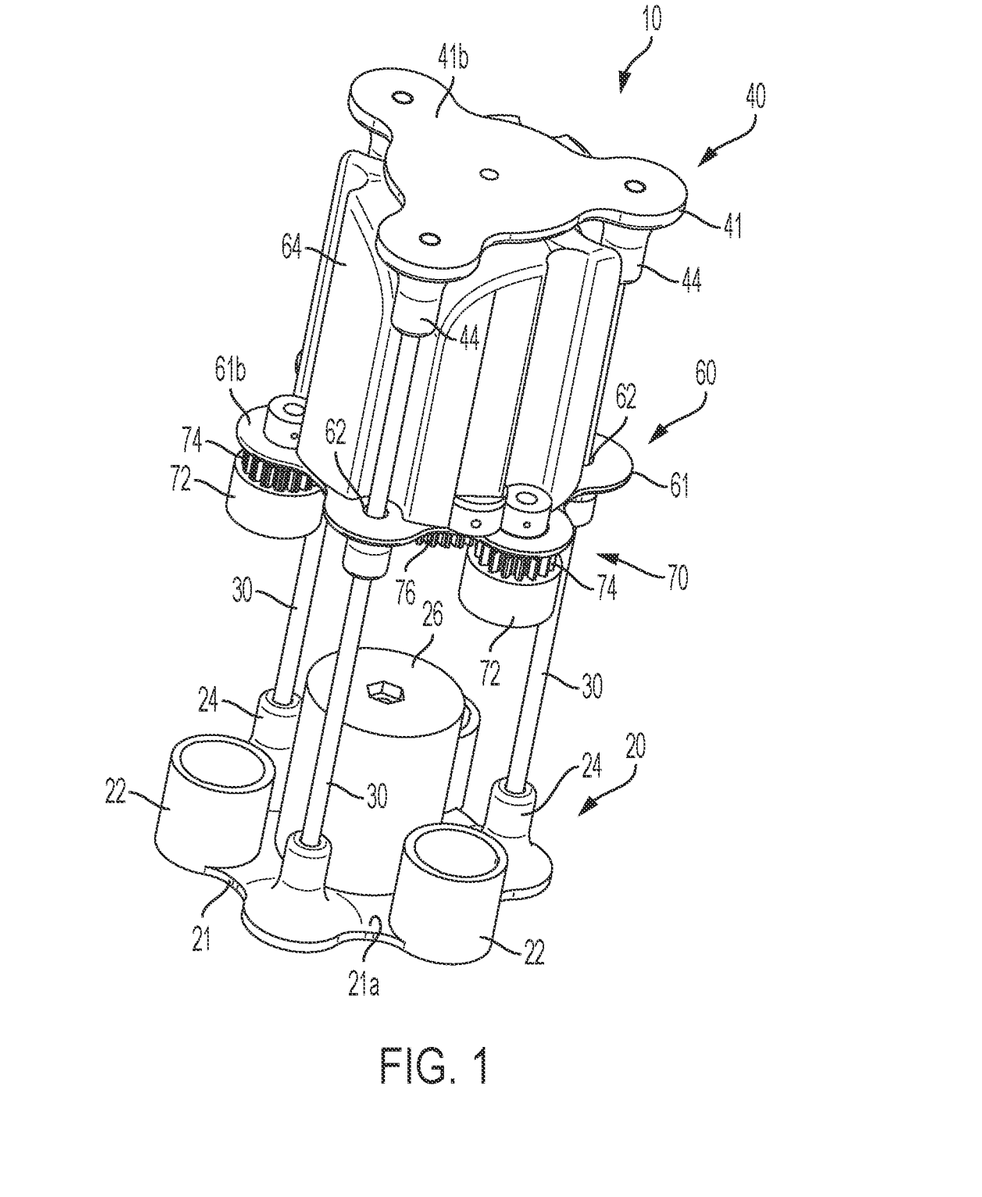
FIG. 1 is a top perspective view of a liquid sampling apparatus, according to some embodiments of the present inventive concept.
Figure 2:
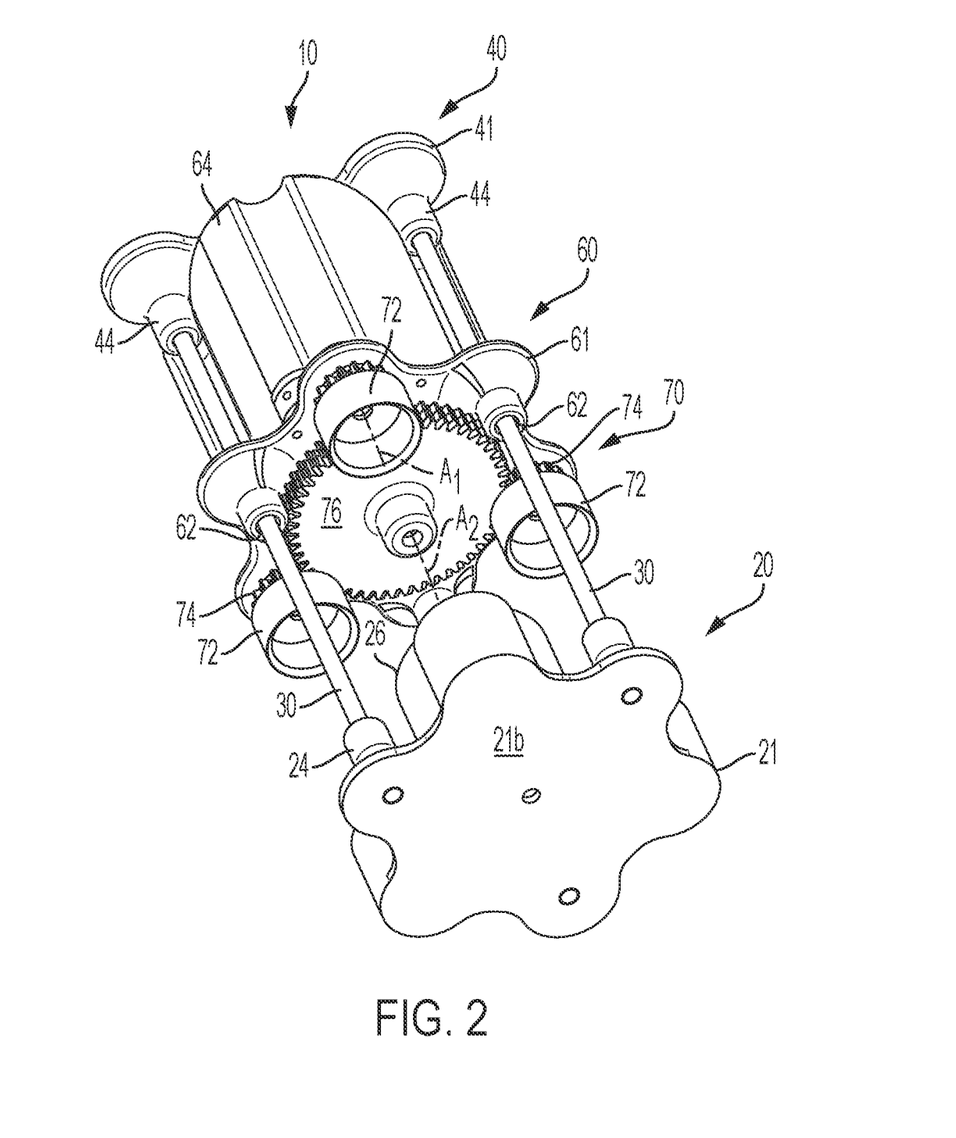
FIG. 2 is a bottom perspective view of the liquid sampling apparatus of FIG. 1.
Figure 3:
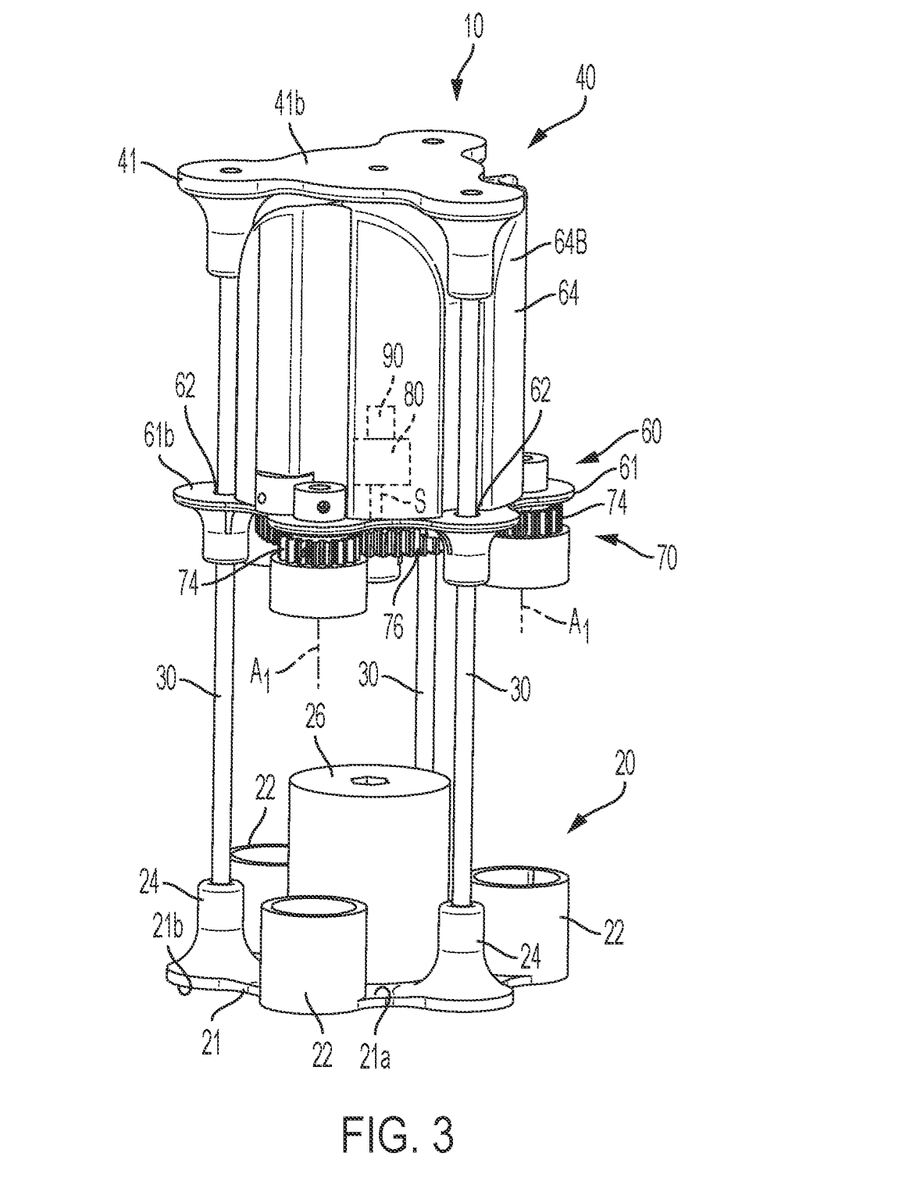
FIG. 3 is another top perspective view of the liquid sampling apparatus of FIG. 1.

A liquid sampling apparatus and method will be described with reference to the figures. Referring to FIGS. 1-3, the illustrated liquid sampling apparatus 10 includes a base 20, an upper portion 40, and an intermediate portion 60 that is movable between the base 20 and the upper portion 40. The illustrated base 20 includes a plate 21 with opposite first and second sides 21a, 21b. A plurality of bottle holders 22 extend outwardly from the plate first surface 21a, as illustrated. Each bottle holder 22 is configured to removably receive a sample bottle B (FIGS. 4-9) therein. Although three bottle holders 22 are illustrated, embodiments of the present inventive concept are not limited thereto. Various numbers of bottle holders 22, including a single bottle holder, may be utilized. Moreover, the bottle holders 22 may all be configured to hold the same size sample bottle, or the bottle holders 22 may be configured to hold different size sample bottles. The liquid sampling apparatus can be modified to accommodate varying bottle sizes and configurations.

The liquid sampling apparatus 10 includes an upper portion 40 and a plurality of elongate rods 30 coupling the base 20 to the upper portion 40 in spaced-apart relation to each other, as illustrated. Although three elongate rods 30 are illustrated, embodiments of the present inventive concept are not limited thereto. Various numbers of elongate rods 30, including a single rod, may be utilized. Moreover, the elongate rods 30 may each have various cross-sectional configurations. Embodiments of the present inventive concept are not limited to the illustrated configuration and arrangement of the rods 30.

A plurality of bosses 24 extend outwardly from the base plate first side 21a, as illustrated. Each boss 24 is configured to receive and secure a respective end of an elongate rod 30. Each boss 24 may secure the respective end of an elongate rod 30 in various ways, without limitation. For example, in some embodiments, the end of an elongate rod 30 may be threadingly engaged within a boss 24. In other embodiments, the end of an elongate rod 30 may be press or friction fit within a boss 24, or may be welded therein. In addition, various other ways of securing the rods 30 to the base plate 21 may be utilized without limitation.

The upper portion 40 includes a plate 41 with opposite first and second sides 41a, 41b. A plurality of bosses 44 extend outwardly from the plate first side 41a, as illustrated. Each boss 44 is configured to receive and secure a respective end of an elongate rod 30. Each boss 44 may secure the respective end of an elongate rod 30 in various ways, without limitation. For example, in some embodiments, the end of an elongate rod 30 may be threadingly engaged within a boss 44. In other embodiments, the end of an elongate rod 30 may be press or friction fit within a boss 44, or may be welded therein. In addition, various other ways of securing the rods 30 to the upper portion plate 41 may be utilized without limitation.

The intermediate portion 60 is movably secured to the elongate rods 30 between the base 20 and the upper portion 40, as illustrated. The illustrated intermediate portion 60 includes a plate 61 with opposite first and second sides 61a, 61b. Passageways 62 are formed through the intermediate portion plate 61, and a respective rod 30 extends through each passageway 62. As such, the intermediate portion 60 is slidably movable along the rods 30 between the base 20 and the upper portion 40.

The intermediate portion 60 includes a float 64 that is configured to provide buoyancy to the liquid sampling apparatus 10 such that the liquid sampling apparatus 10 floats on a liquid surface with the upper portion 40 above the surface and with the base 20 and intermediate portion 60 submerged, as illustrated in FIGS. 5-8. In the illustrated embodiment, the float 64 is secured to the second side 61b of the intermediate portion plate 61. When the liquid sampling apparatus 10 is lowered into a body of liquid, such as a body of water (e.g., a river, a lake, a pond, etc.), the apparatus 10 is configured to float on the liquid surface because of the float 64. However, the float configuration is such that, when the apparatus 10 is floating on a liquid surface, the base 20 is submerged beneath the liquid surface such that the sample bottles B within the various holders 22 and the caps C are always submerged. As such, the caps C can be removed from and resecured to the sample bottles B entirely beneath the liquid surface to prevent any contaminants from the air above the surface entering the sample bottles B. In the illustrated embodiment, the base 20 includes a weight or ballast 26 that facilitates further submerging of the base 20 and sample bottles B held therewithin beneath the liquid surface when the caps C are removed.

The intermediate portion 60 also includes a cap engagement apparatus 70 that is configured to remove the cap C from each sample bottle B prior to obtaining a liquid sample, and to resecure the cap C to the sample bottle B after the liquid sample has been obtained. In the illustrated embodiment, the cap engagement apparatus 70 includes a plurality of sockets 72 that are configured to releasably engage each respective cap C of a sample bottle. Each socket 72 is sized and configured for a friction fit with each cap such that, when a cap C is removed from a sample bottle B by the socket, the cap C is retained within the socket 72 sufficiently to prevent dislodgement therefrom.

Each socket 72 is rotatable and is configured to threadingly remove a respective cap C from a sample bottle B and to threadingly resecure the cap C to the sample bottle B. In the illustrated embodiment, each socket 72 includes a respective gear 74 that meshes with a primary gear 76 such that rotation of the primary gear 76 about its rotational axis causes each socket 72 to rotate about its rotational axis. As such, the caps C are removed from, and resecured to, the sample bottles B in unison. Each gear 74, and respective socket 72, is rotatably secured to the first side 61a of the intermediate portion plate 61, as illustrated. The rotational axis of each gear 74 is indicated by $A_1$. The primary gear 76 is rotatably secured to the first side 61a of the intermediate portion plate 61, as illustrated. The rotational axis of the primary gear 76 is indicated by $A_2$.

Figure 10:
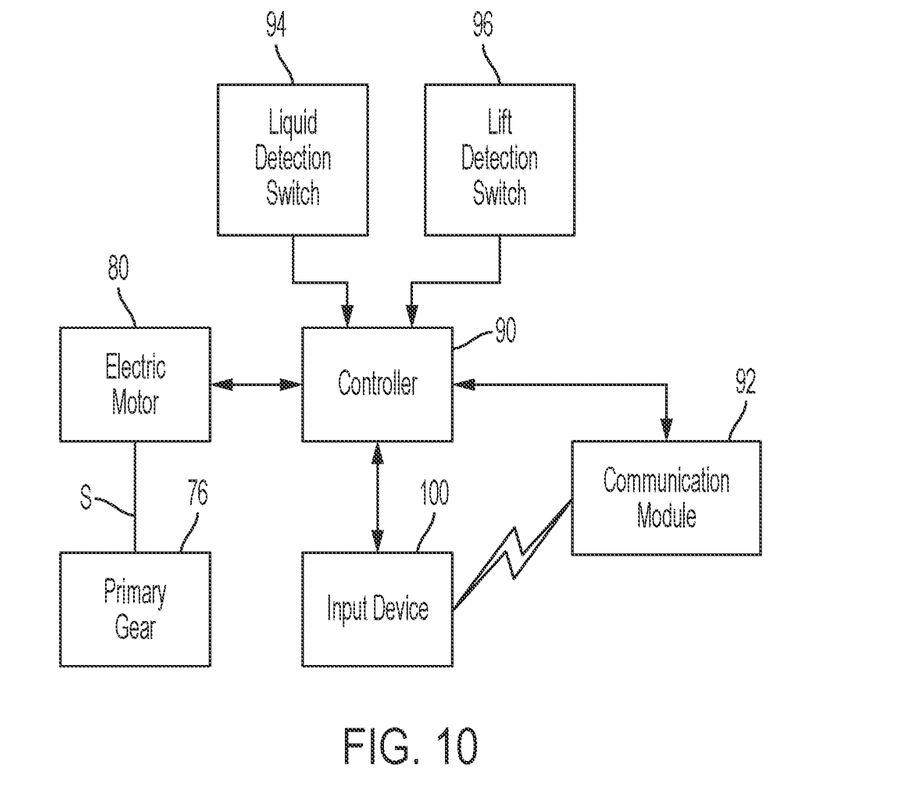
FIG. 10 is a diagram of the various electronic components that can be utilized with the liquid sampling apparatus of FIGS. 1-9.

In the illustrated embodiment, the intermediate portion 60 of the apparatus 10 includes an electric motor 80 that is operably associated with the primary gear 76 via a shaft S (FIGS. 3 and 10) and configured to rotate the primary gear about its rotational axis $A_2$, so as to cause the cap engagement apparatus to remove and resecure caps C from/to the sample bottles B. An electronic controller 90 (FIGS. 3 and 10) is in electronic communication with the electric motor 80 and is configured to control operation of the electric motor 80 in response to a control signal from an input device 100 (FIG. 10). In the illustrated embodiment, the electric motor 80 and controller 90 are located within the body 64B of the float. The interior of the float body 64B provides a sealed, protective environment for the electric motor 80 and controller 90 when the apparatus 10 is floating on the surface of a liquid. As such, the electronic components are protected from exposure to the external environment, including the liquid.

In some embodiments, the apparatus 10 includes a communication module 92 (FIG. 10) that is configured to receive, over a wireless link, a control signal from the input device 100. The communication module 92 may also be located within the float body 64B.

In some embodiments, the liquid sampling apparatus 10 includes a liquid detection switch 94 (FIG. 10) that is configured to detect when the liquid sampling apparatus 10 has been lowered into a liquid. The electronic controller 90 is configured to control operation of the electric motor 80 such that the cap engagement apparatus 70 removes the caps C from the sample bottles B in response to a signal received from the liquid detection switch 94 that the liquid sampling apparatus 10 is in the liquid.

In some embodiments, the liquid sampling apparatus 10 may include a lift detection switch 96 (FIG. 10) that is configured to detect when the liquid sampling apparatus 10 is being lifted from the liquid. The electronic controller 90 is configured to control operation of the electric motor 80 such that the cap engagement apparatus 70 resecures the caps C to the sample bottles B in response to a signal received from the lift detection switch 96.

Figure 4:
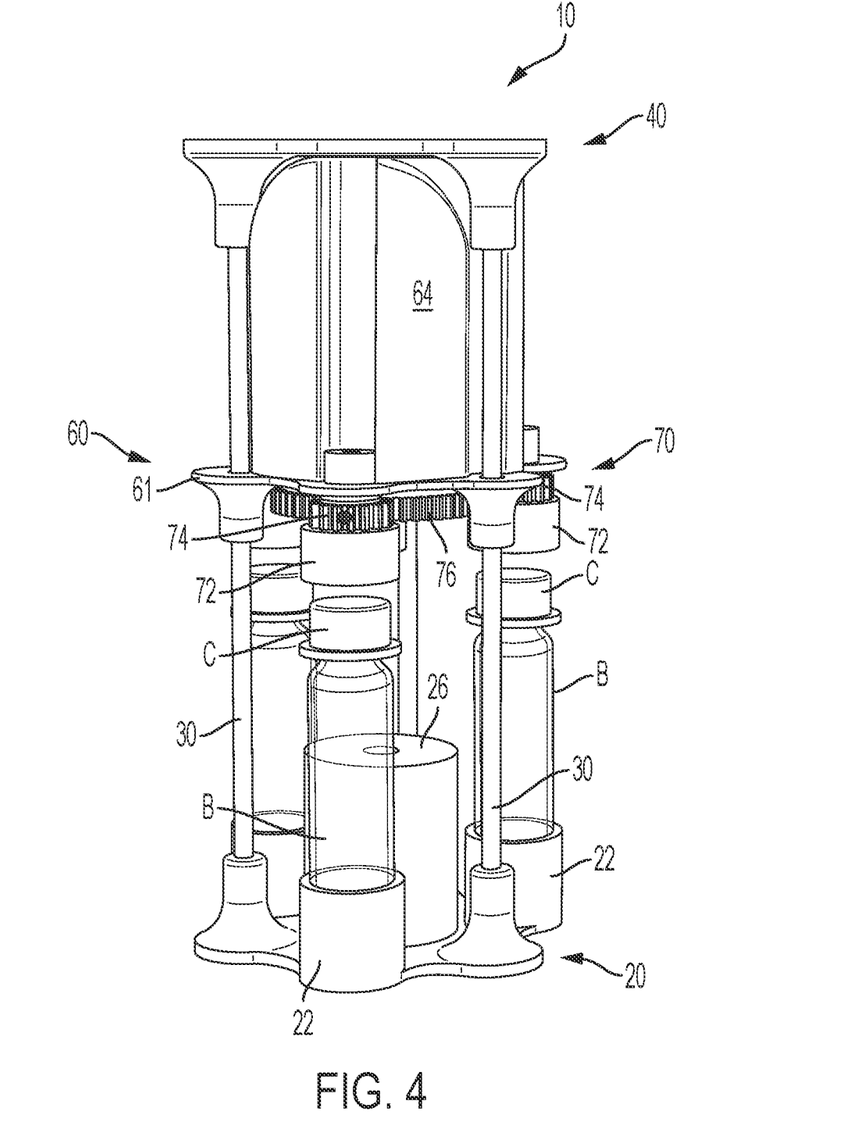
FIG. 4 illustrates the liquid sampling apparatus of FIG. 1 with sample bottles removably secured within respective holders. The sample bottles have caps threadingly secured thereto.
Figure 5:
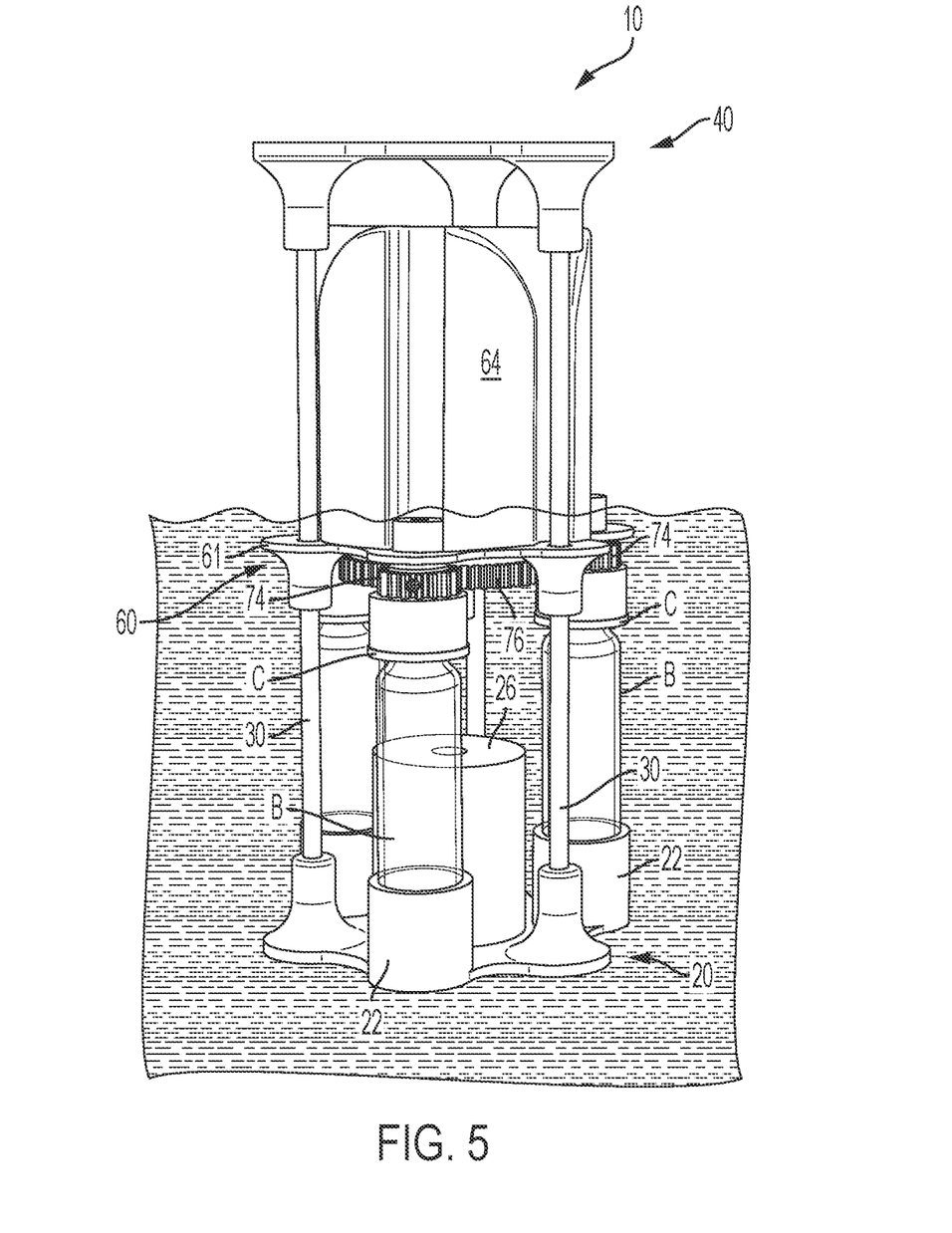
FIG. 5 illustrates the liquid sampling apparatus of FIG. 1 floating in a liquid, such as water, with the bottles and caps submerged in the liquid and illustrating the cap engagement apparatus engaging the bottle caps in preparation for removing the caps from the sample bottles.

Referring now to FIGS. 4-9, operation of the hands-free liquid sampling apparatus 10 will be described. In FIG. 4, sample bottles B are removably secured within the bottle holders 22 and the caps C are secured to the sample bottles B. The intermediate portion 70 slides downwardly such that the sockets 72 releasably engage the respective caps C secured to the sample bottles B. The liquid sampling apparatus is then lifted over and into a body of liquid, such as a body of water (e.g., a river, a lake, a pond, etc.) and floats on the surface of the liquid, as illustrated in FIG. 5. As described above, when the sampling apparatus 10 floats on the surface of a liquid, the base 20 and sample bottles B supported therein are submerged. In addition, the plate 61 of the intermediate portion 60, including the cap engagement apparatus 70 is also submerged such that the caps C are always beneath the surface of the liquid when secured to the sample bottles B and when removed from the sample bottles B.

Figure 6:
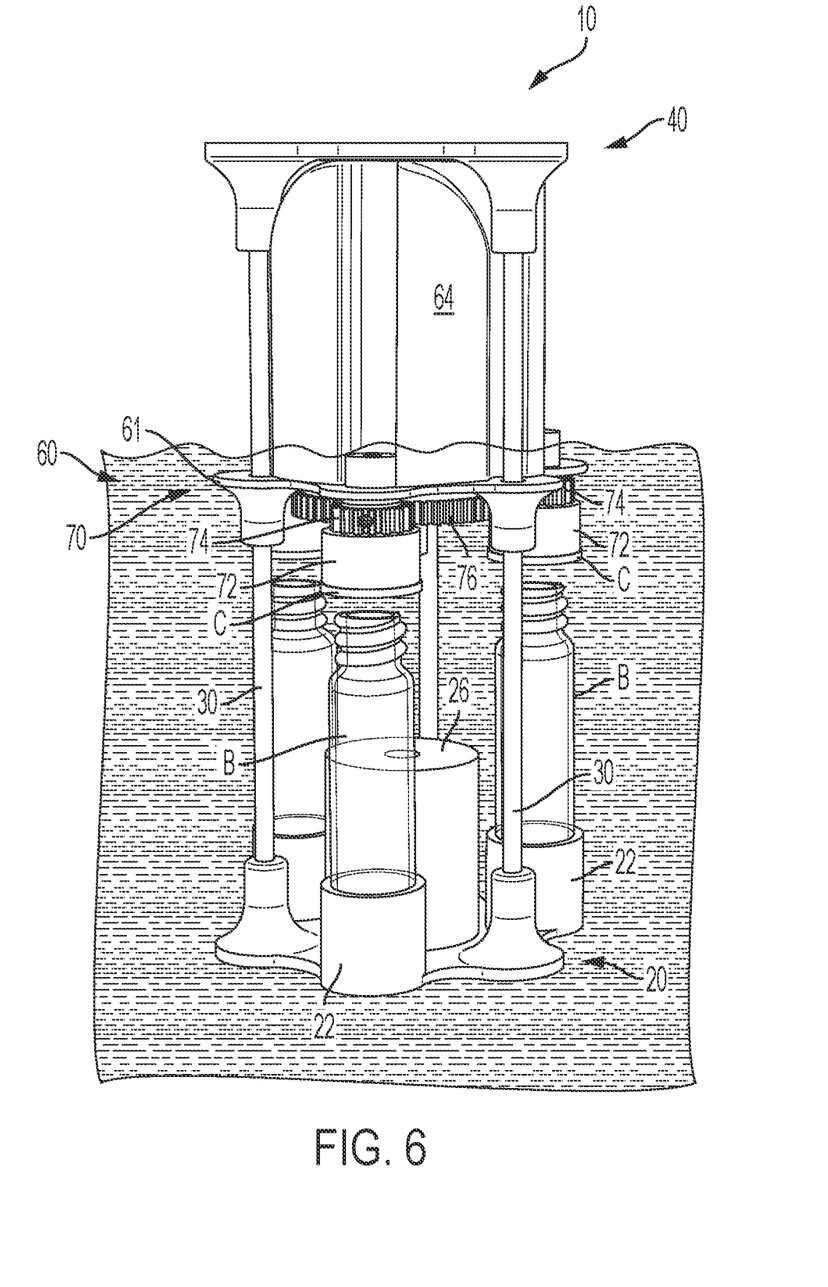
FIG. 6 illustrates the liquid sampling apparatus of FIG. 5 with the caps removed from the bottles while submerged and the base and open sample bottles submerging further under the liquid surface.
Figure 7:
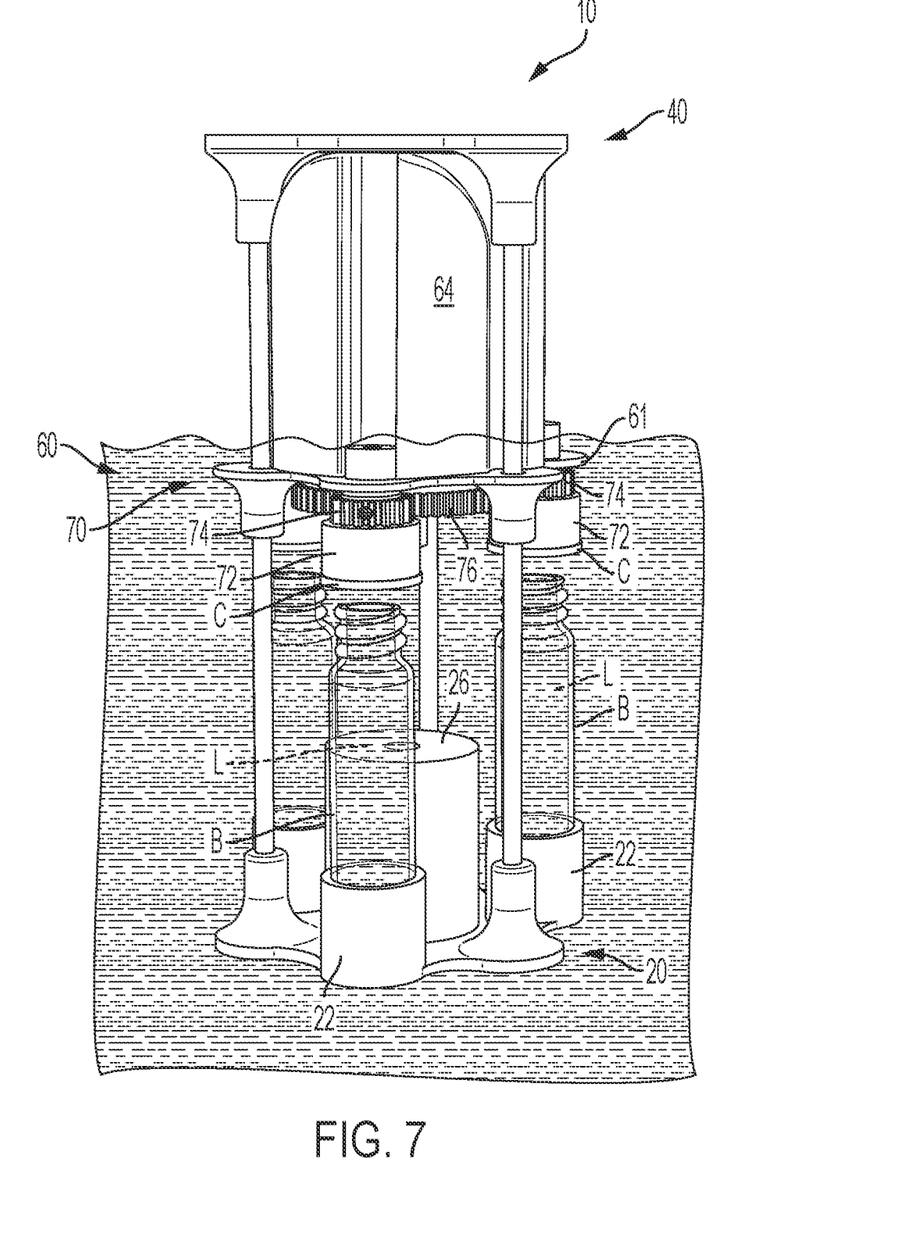
FIG. 7 illustrates the liquid sampling apparatus of FIG. 6 with the sample bottles filled with liquid.
Figure 8:
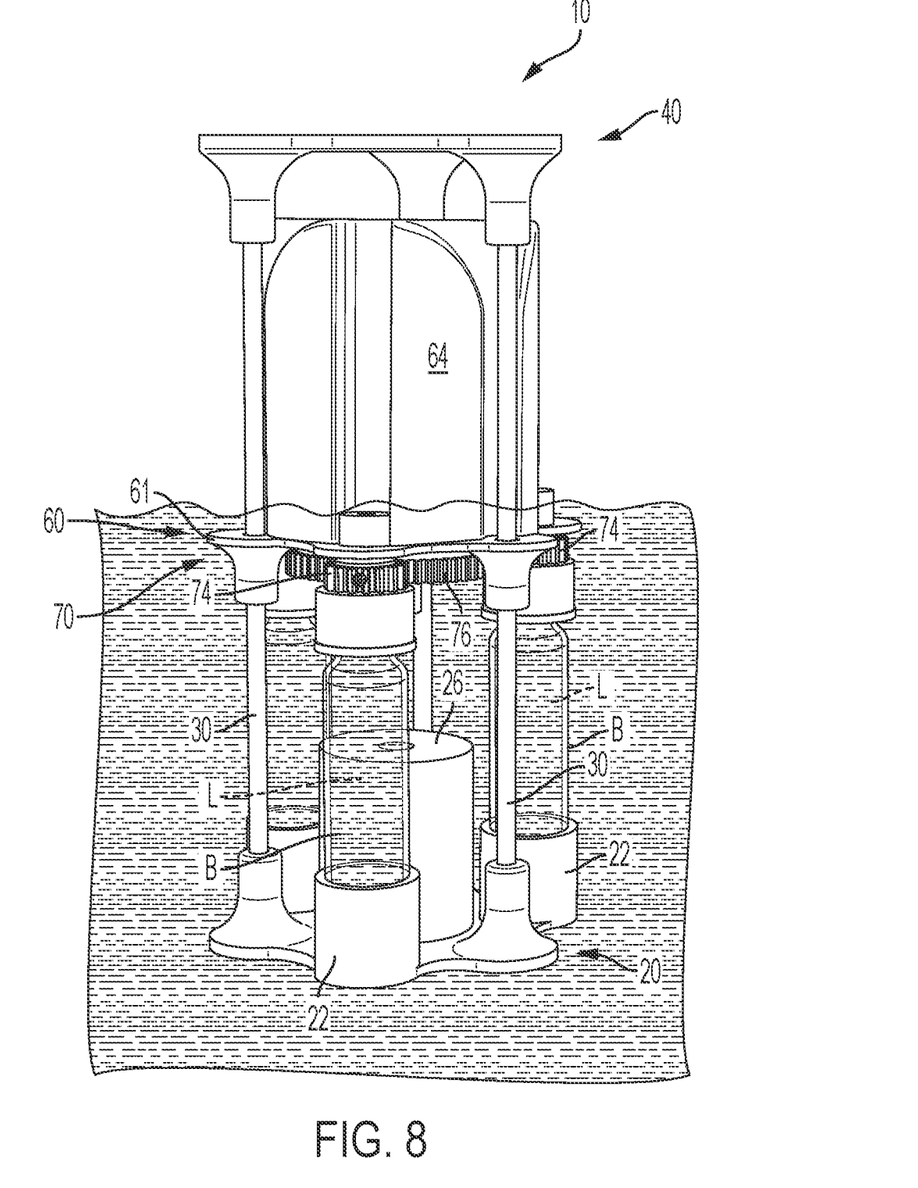
FIG. 8 illustrates the liquid sampling apparatus of FIG. 7 with the caps resecured to the sample bottles by the cap engagement apparatus while the bottles are still submerged.
Figure 9:
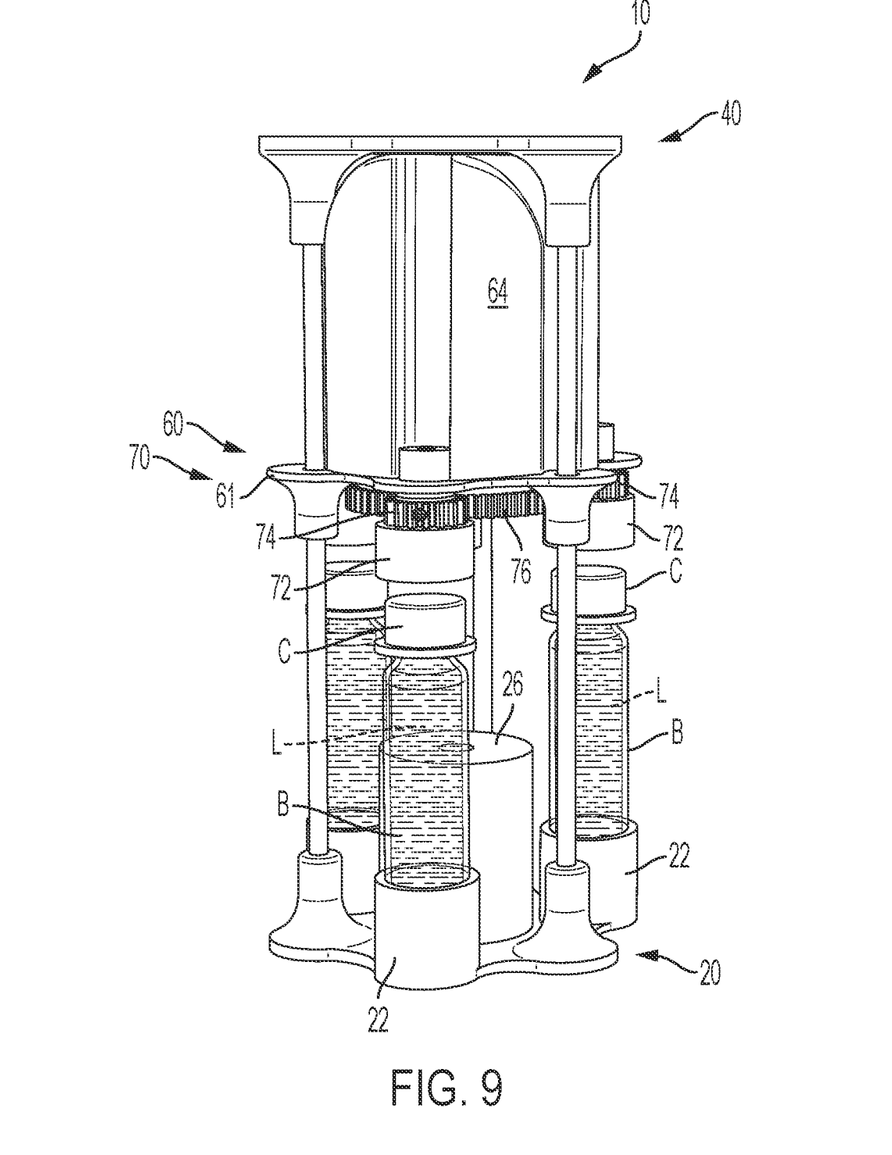
FIG. 9 illustrates the liquid sampling apparatus of FIG. 8 after the apparatus has been lifted from the liquid, and with the sample bottles ready to be removed from the holders.

In FIG. 6, the cap engagement apparatus 70 has removed the caps C from the sample bottles B, and the weight 26 causes the base 20 and sample bottles B supported therein to submerge slightly more. The sample bottles B fill with liquid L, as illustrated in FIG. 7. The intermediate portion 60 then moves downwardly so that the sockets 72 containing the caps C engage the respective tops of the sample bottles B. The cap engagement apparatus 70 is then operated such that the sockets 72 threadingly resecure the caps C to the sample bottles B (FIG. 8). This downward motion of the intermediate portion 60 is caused by the upward motion of the sampling apparatus 10 as it is being lifted out of the liquid (i.e., the intermediate portion and the cap engagement apparatus move downwardly under the force of gravity to engage the sample bottles). However, the caps C are resecured to the sample bottles B before the tops of the sample bottles B reach the surface of the liquid. This prevents any contamination from the air from entering the open sample bottles B. FIG. 9 illustrates the sampling apparatus 10 removed from the liquid and with the intermediate portion 60 raised upwardly from the sample bottles B such that the sample bottles B with the liquid L inside can be removed from the respective holders 22.

The foregoing is illustrative of the present invention and is not to be construed as limiting thereof Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A liquid sampling apparatus, comprising:
a base comprising at least one bottle holder;
an upper portion;
at least one elongate rod coupling the base and the upper portion in spaced-apart relation to each other; and
an intermediate portion movably secured to the at least one elongate rod between the base and the upper portion, the intermediate portion comprising:
a float configured to provide buoyancy to the liquid sampling apparatus such that the liquid sampling apparatus floats on a liquid surface; and
a cap engagement apparatus configured to remove a cap from a bottle supported within the at least one bottle holder, and to resecure the cap to the bottle, wherein the cap engagement apparatus comprises a socket configured to releasably engage the cap.

2. The liquid sampling apparatus of claim 1, wherein, when the liquid sampling apparatus is floating on the liquid surface, the base is configured to submerge beneath the liquid surface such that the bottle fills with the liquid in response to the cap engagement apparatus removing the cap from the bottle.

3. The liquid sampling apparatus of claim 2, wherein the base comprises a ballast that facilitates submerging of the base beneath the liquid surface.

4. The liquid sampling apparatus of claim 2, wherein, when the liquid sampling apparatus is lifted from the liquid surface, the cap engagement apparatus is configured to move downwardly to engage the bottle and resecure the cap to the bottle.

5. The liquid sampling apparatus of claim 1-4, wherein the socket is rotatable and configured to threadingly remove the cap from the bottle and to threadingly resecure the cap to the bottle.

6. The liquid sampling apparatus of claim 5, wherein the socket comprises a gear that meshes with a primary gear associated with the intermediate portion such that rotation of the primary gear about its rotational axis causes the socket to rotate about its rotational axis.

7. The liquid sampling apparatus of claim 6, wherein the intermediate portion comprises an electric motor configured to rotate the primary gear about its rotational axis, and an electronic controller operable to control operation of the electric motor in response to a control signal from an input device.

8. The liquid sampling apparatus of claim 7, further comprising a communication module configured to receive, over a wireless link, the control signal from the input device.

9. The liquid sampling apparatus of claim 7, further comprising:
a liquid detection switch configured to detect when the liquid sampling apparatus is in the liquid; and
wherein the electronic controller controls operation of the electric motor such that the cap engagement apparatus removes the cap from the bottle in response to a signal received from the liquid detection switch.

10. The liquid sampling apparatus of claim 7, further comprising:
a lift detection switch configured to detect when the liquid sampling apparatus is lifted from the liquid; and
wherein the electronic controller controls operation of the electric motor such that the cap engagement apparatus resecures the cap to the bottle in response to a signal received from the lift detection switch.

11. The liquid sampling apparatus of claim 7, wherein the electric motor and the electronic controller are located within a body of the float.

12. The liquid sampling apparatus of claim 1, wherein the base comprises a plurality of bottle holders, and wherein the cap engagement apparatus is configured to remove the cap from each respective bottle supported within a bottle holder, and to resecure the cap to each respective bottle.

13. A liquid sampling apparatus, comprising:
a base comprising at least one bottle holder;
an upper portion;
at least one elongate rod coupling the base and the upper portion in spaced-apart relation to each other;
an intermediate portion movably secured to the at least one elongate rod between the base and the upper portion, the intermediate portion comprising:
a float configured to provide buoyancy to the liquid sampling apparatus such that the liquid sampling apparatus floats on a liquid surface; and
a cap engagement apparatus configured to remove a cap from a bottle supported within the at least one bottle holder, and to resecure the cap to the bottle, the cap engagement apparatus comprising a socket configured to releasably engage the cap, an electric motor configured to rotate the socket, and an electronic controller operable to control operation of the electric motor; and
a liquid detection switch configured to detect when the liquid sampling apparatus is in the liquid;
wherein the electronic controller controls operation of the electric motor such that the cap engagement apparatus removes the cap from the bottle in response to a signal received from the liquid detection switch.

14. The liquid sampling apparatus of claim 13, wherein, when the liquid sampling apparatus is floating on the liquid surface, the base is configured to submerge beneath the liquid surface such that the bottle fills with the liquid in response to the cap engagement apparatus removing the cap from the bottle.

15. The liquid sampling apparatus of claim 14, wherein, when the liquid sampling apparatus is lifted from the liquid surface, the cap engagement apparatus is configured to move downwardly to engage the bottle and resecure the cap to the bottle.

16. The liquid sampling apparatus of claim 13, wherein the socket is rotatable and configured to threadingly remove the cap from the bottle and to threadingly resecure the cap to the bottle, wherein the socket comprises a gear that meshes with a primary gear associated with the intermediate portion such that rotation of the primary gear about its rotational axis by the electric motor causes the socket to rotate about its rotational axis.

17. The liquid sampling apparatus of claim 13, wherein the electric motor and the electronic controller are located within a body of the float.

18. The liquid sampling apparatus of claim 13, wherein the base comprises a plurality of bottle holders, and wherein the cap engagement apparatus is configured to remove the cap from each respective bottle supported within a bottle holder, and to resecure the cap to each respective bottle.

19. A liquid sampling method, comprising: lowering a floatable sampling apparatus into a liquid, the floatable sampling apparatus comprising a base supporting a bottle, and a rotatable cap engagement apparatus configured to threadingly remove a cap from the bottle and to threadingly resecure the cap to the bottle; threadingly removing the cap from the bottle via the rotatable cap engagement apparatus, thereby causing the bottle to fill with the liquid; and lifting the floatable sampling apparatus from the liquid, thereby causing the rotatable cap engagement apparatus to move downwardly to engage the bottle and threadingly resecure the cap to the bottle.

* * * * *